United States Patent
Starr et al.

[11] Patent Number: 6,045,576
[45] Date of Patent: Apr. 4, 2000

[54] SEWING RING HAVING INCREASED ANNULAR COAPTATION

[75] Inventors: Albert Starr, Portland, Oreg.; Robert Stobie, Mission Viejo; Michael N. Helmus, Long Beach, both of Calif.

[73] Assignee: Baxter International Inc., Deerfield, Ill.

[21] Appl. No.: 08/932,818

[22] Filed: Sep. 16, 1997

[51] Int. Cl.[7] .................................................. A61F 2/24
[52] U.S. Cl. ............................................................ 623/2
[58] Field of Search .................................. 623/1, 2, 900; 606/151, 153

[56] References Cited

U.S. PATENT DOCUMENTS

| | | |
|---|---|---|
| 3,548,417 | 12/1970 | Kischer . |
| 4,535,483 | 8/1985 | Klawitter et al. . |
| 4,705,516 | 11/1987 | Barone et al. . |
| 4,799,930 | 1/1989 | Knoch et al. . |
| 4,865,600 | 9/1989 | Carpentier et al. . |
| 4,923,465 | 5/1990 | Knoch et al. . |
| 4,995,881 | 2/1991 | Knoch et al. . |
| 5,035,709 | 7/1991 | Wieting et al. . |
| 5,071,431 | 12/1991 | Sauter et al. ................................ 623/2 |
| 5,178,633 | 1/1993 | Peters .......................................... 623/2 |
| 5,360,014 | 11/1994 | Sauter et al. . |
| 5,397,346 | 3/1995 | Walker et al. . |
| 5,397,348 | 3/1995 | Campbell et al. . |
| 5,489,296 | 2/1996 | Love et al. . |
| 5,584,879 | 12/1996 | Reimold et al. ............................ 623/2 |
| 5,612,885 | 3/1997 | Love . |
| 5,755,783 | 5/1998 | Stobie et al. ................................ 623/2 |
| 5,776,188 | 7/1998 | Shepherd et al. .......................... 623/2 |

FOREIGN PATENT DOCUMENTS

| | | |
|---|---|---|
| 0 355 323 B1 | 6/1989 | European Pat. Off. . |
| WO 89/00841 | 2/1989 | WIPO . |
| WO 91/17721 | 11/1991 | WIPO . |
| WO 92/12690 | 8/1992 | WIPO . |
| WO 93/01760 | 2/1993 | WIPO . |
| WO 95/16408 | 6/1995 | WIPO . |
| WO 95/16412 | 6/1995 | WIPO . |
| WO 96/40010 | 12/1996 | WIPO . |
| WO 97/10757 | 3/1997 | WIPO . |

Primary Examiner—Bruce E. Snow
Attorney, Agent, or Firm—Guy L. Cumberbatch; James W. Inskeep; Debra D. Condino

[57] ABSTRACT

A sewing ring for implantation of prosthetic heart valves has a compliant ring member made of a plurality of cells. The ring member may be silicon rubber and the cells defined within outer walls and inner ribs. A biocompatible fabric covering surrounds at least an outer portion of the ring member, and the assembly mounts to a mechanical or tissue-type prosthetic heart valve. The ring member has a radial dimension and cross-sectional area sufficient to ensure a large coaptation area between the sewing ring and the annulus tissue so as to enable adequate attachment of the valve without load distributing devices such as pledgets. A version of the sewing ring for attachment to the mitral annulus includes a curved coaptation edge, while another embodiment for attachment to the aortic annulus has a tapered outer edge with increased radial and axial dimensions. The sewing ring eliminates the need for pledgets, reduces the number of sutures required, lessens the potential for decubitous ulceration, and provides a better seal against perivalvular leakage. Moreover, the aortic valve sewing ring is sufficiently flexible and large to be able to be placed intra- or supra-annularly, as the surgeon deems best for the patient.

21 Claims, 13 Drawing Sheets

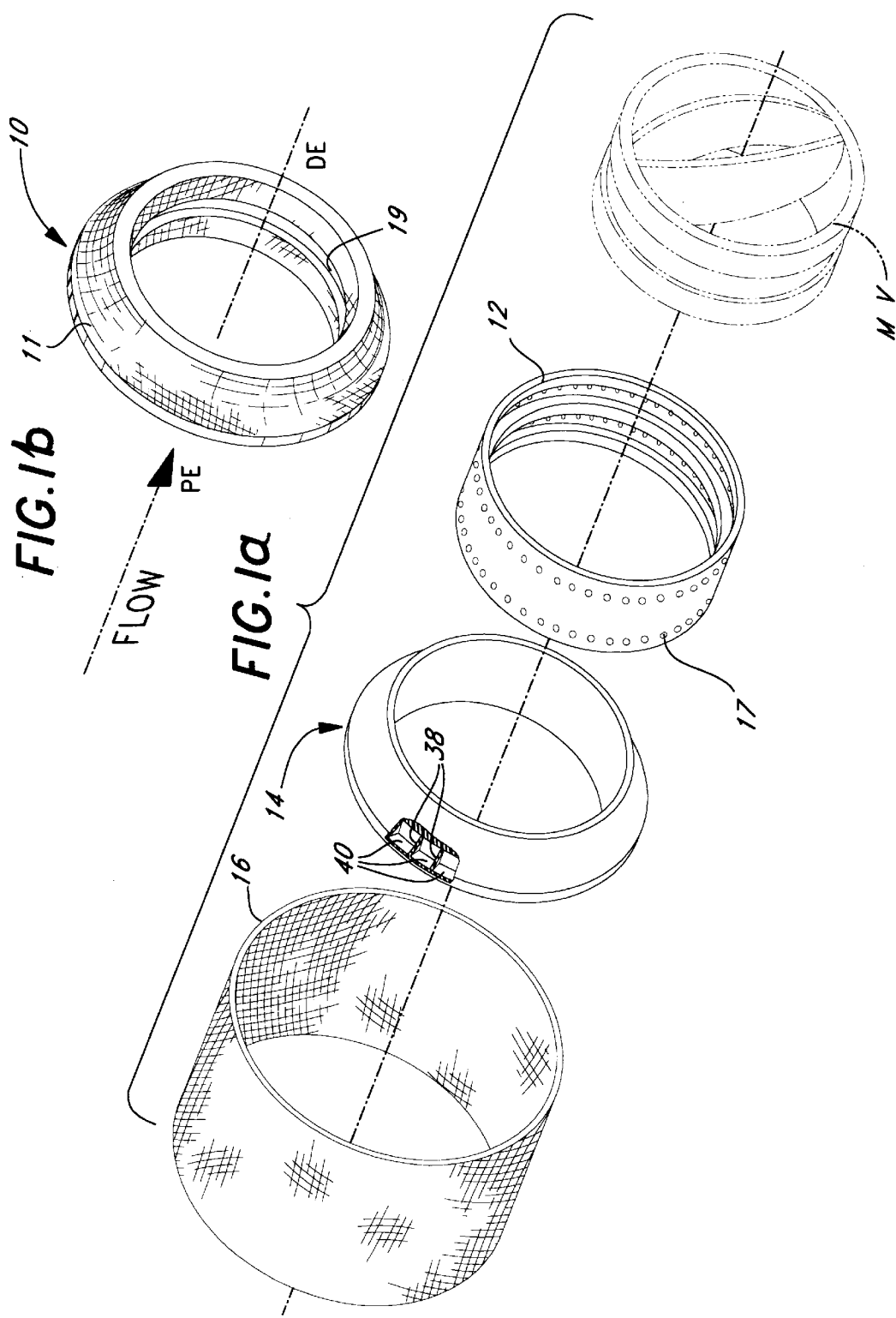

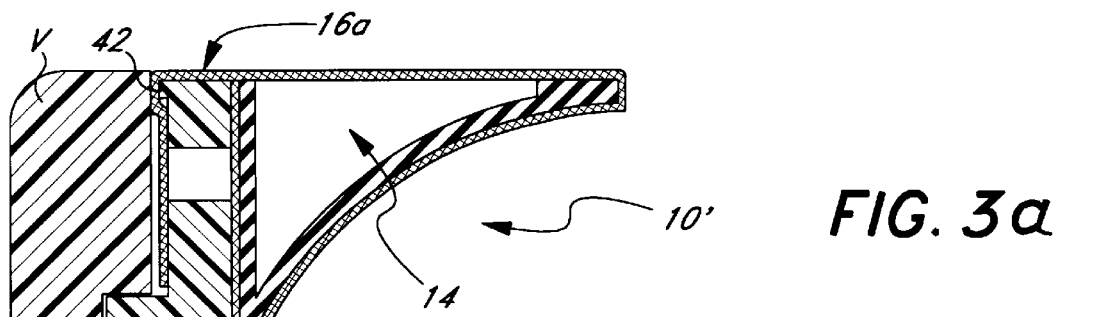
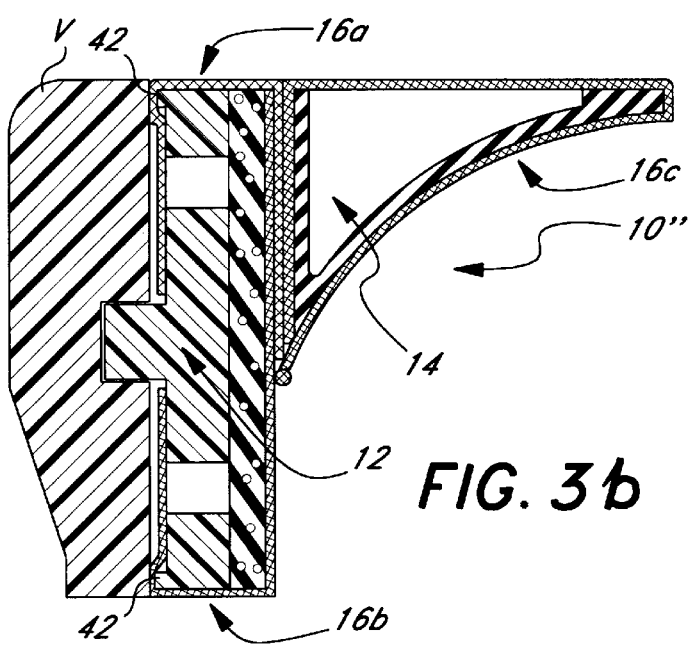
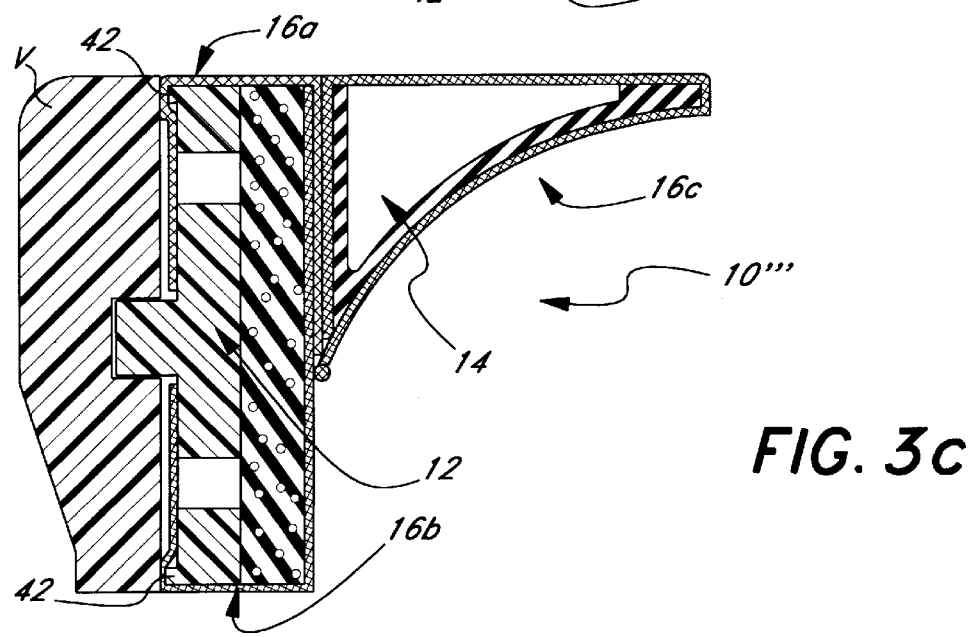
FIG. 3a
FIG. 3b
FIG. 3c

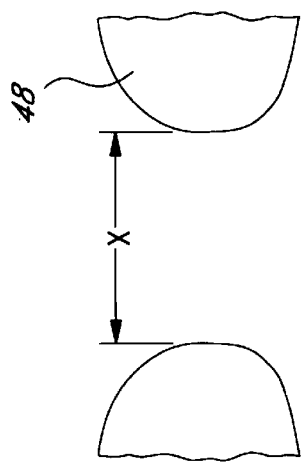
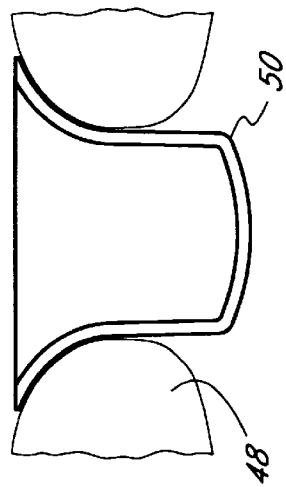
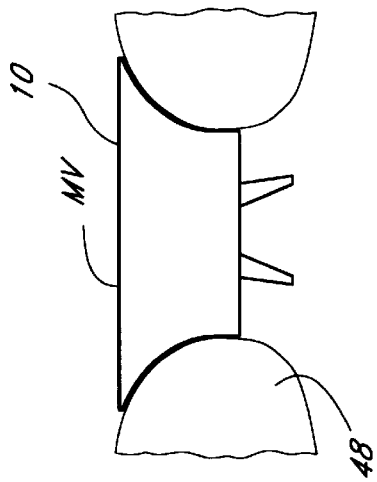
FIG.4a   FIG.4b   FIG.4c
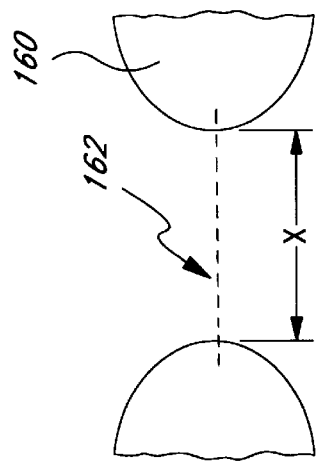
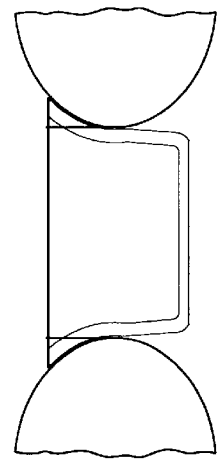
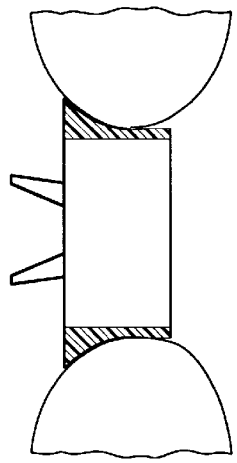
FIG.10a   FIG.10b   FIG.10c

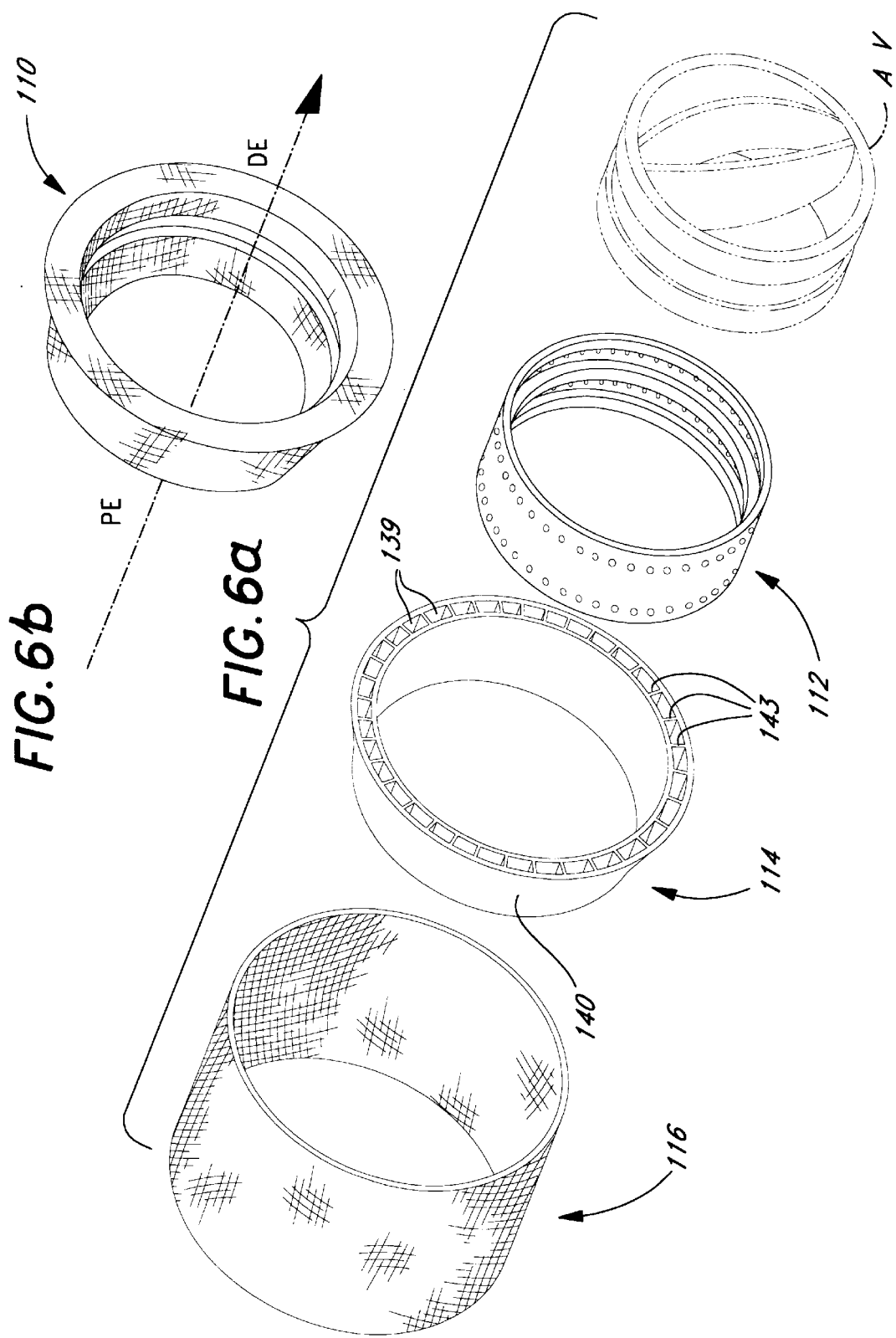

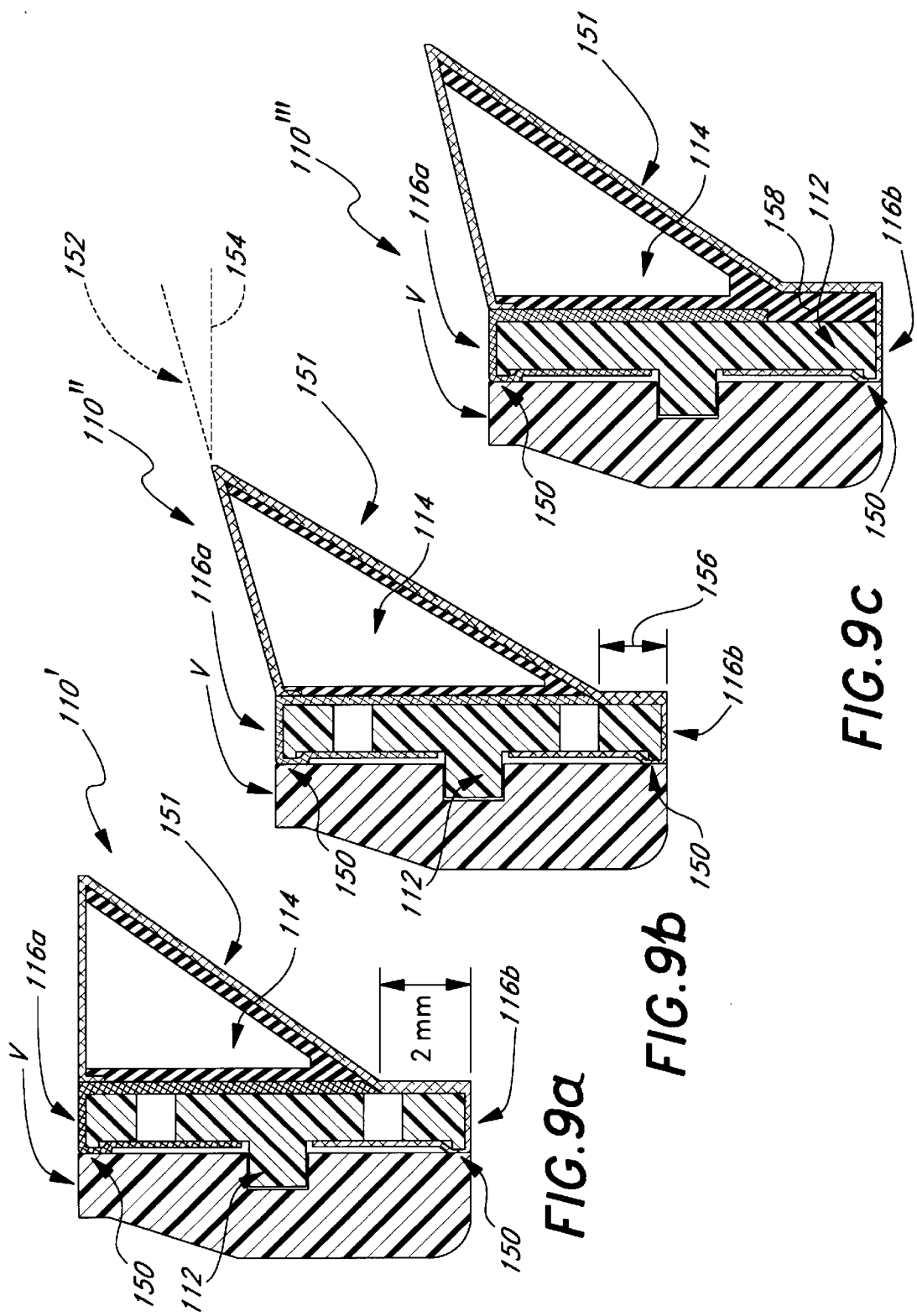

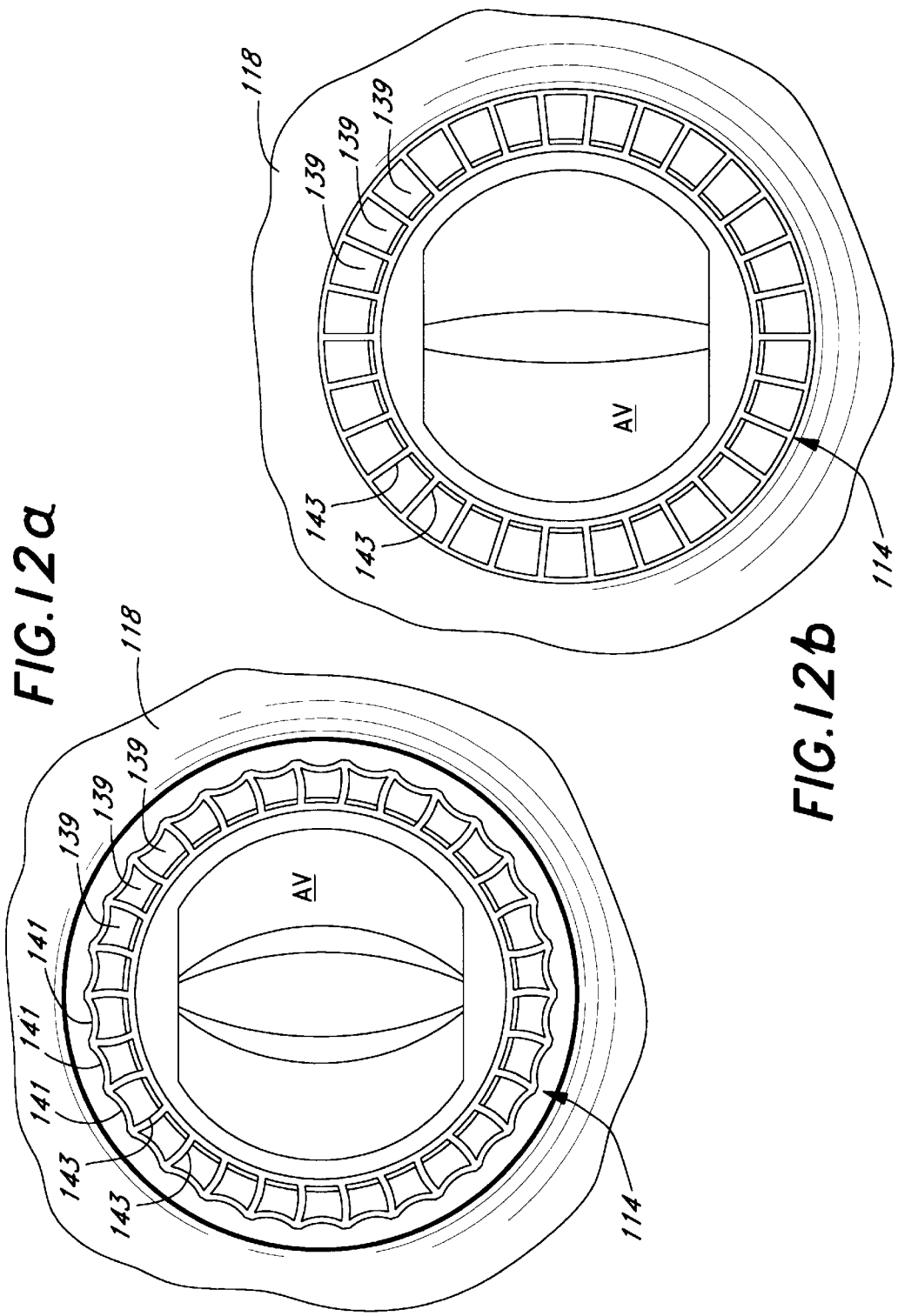

SEWING RING HAVING INCREASED ANNULAR COAPTATION

FIELD OF THE INVENTION

The present invention relates generally to medical devices and particularly to heart valve prostheses having an improved sewing ring which facilitates valve coaptation with surrounding tissue, improves the valve attachment methodology and increases valve stability when the prostheses is implanted in the heart.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves, although repair or replacement of the aortic or mitral valves are most common because they reside in the left side of the heart where pressures are the greatest.

Two primary types of heart valve replacements or prostheses are known. One is a mechanical-type heart valve which uses a ball and cage arrangement or a pivoting mechanical closure to provide unidirectional blood flow. The other is a tissue-type or "bioprosthetic" valve which is constructed with natural-tissue valve leaflets which function much like a natural human heart valve's, imitating the natural action of the flexible heart valve leaflets which seal against each other to ensure the one-way blood flow. In both types of prosthetic valves, a biocompatible cloth covered suture ring on the valve body (mechanical) or stent (tissue-type) provides a platform for attaching the valve to the annulus of the particular valve being replaced.

The valves of the heart separate chambers therein, and are each mounted in an annulus therebetween. The annuluses comprise dense fibrous rings attached either directly or indirectly to the atrial and ventricular muscle fibers. In a valve replacement operation, the damaged leaflets are excised and the annulus sculpted to receive a replacement valve. Ideally the annulus presents relatively healthy tissue which can be formed by the surgeon into a uniform ledge projecting into the orifice left by the removed valve. The time and spacial constraints imposed by surgery, however, often dictate that the shape of the resulting annulus is less than perfect for attachment of a sewing ring. Moreover, the annulus may be calcified as well as the leaflets and complete annular debridement, or removal of the hardened tissue, results in a larger orifice and less declined annulus ledge to which to attach the sewing ring. In short, the contours of the resulting annulus vary widely after the natural valve has been excised.

Conventional placement of the valve is intra-annular, with the valve body deep within the narrowest portion of the annulus to enhance any seal effected by the sewing ring/suture combination and reduce the chance of perivalvular leakage. Surgeons report using at least 30 simple sutures or 20 mattress-type sutures to prevent leakage. Mattress sutures are more time consuming and essentially comprise double passes of the needle through the tissue with one knot.

The four valves separate each ventricle from its associated atrium, or from the ascending aorta (left ventricle) or pulmonary artery (right ventricle). After the valve excision, the annulus generally comprises a ledge extending into and defining the orifice between the respective chambers. Prosthetic valves may attach on the upstream or downstream sides of the annulus ledge, but outside of the ventricles to avoid interfering with the large contractions therein. Thus, for example, in the left ventricle a prosthetic valve is positioned on the inflow side of the mitral annulus (in the left atrium), or on the outflow side of the aortic annulus (in the ascending aorta). Besides the differing anatomies of the mitral and aortic annuluses, the pressures exerted on the attachment sutures differ as well. The highest pressures to which the sutures are subjected in use is in the backflow half of the flow cycle when the valve closes. In systole, the left ventricle contracts to push blood through the body's circulatory system and the mitral valve is forced closed by pressures of up to 140 mm Hg. Because the prosthetic mitral valve is attached on the inflow side of the annulus opposite the ventricle chamber, the sutures are placed in direct tension. In contrast, the backflow pressure of the ascending aorta on the aortic valve is much less, and in any event the back pressure pushes the prosthetic valve against the aortic annulus so that the attaching sutures are not in tension. The end result is that care must be taken so that the mitral valve is more securely attached, and pledgets are conventionally used in conjunction with sutures in both aortic and mitral implantations to avoid a "cheesewire" effect on the tissue. Pledgets are small pieces of biocompatible fabric attached to each individual suture that are positioned within the loop of the suture between the suture and the tissue to prevent the suture when placed in tension from cutting into the tissue.

Naturally, the implantation of a prosthetic heart valve, either a mechanical valve or a bioprosthetic valve (i.e., "tissue" valve), requires a great deal of skill and concentration given the delicate nature of the native heart tissue, the spatial constraints of the surgical field and the criticality of achieving a secure and reliable implantation. It is of equal importance that the valve itself have characteristics that promote a long valve life and that have minimal impact on the physiological makeup of the heart environment.

Given the uneven nature of the annuluses, the design of the sewing ring and the method with which the sewing ring is fixed into place are perhaps the most crucial aspects of prosthetic heart valve implantation. Accordingly, an optimum sewing ring design contemplates a blend between structure highly complimentary to the valve annulus tissue and a valve attachment platform that simplifies the implantation procedure for the surgeon. Although prior art sewing ring designs are widely varied and numerous, until the design of the present invention, attempts to effectively blend improved structure/tissue compatibility with a convenient "surgeon friendly" sewing platform have been largely unsuccessful.

Many prior art sewing rings are designed to take up little space so as to increase the potential orifice opening for the valve within. One example of a prior art sewing ring may be found in U.S. Pat. No. 5,397,348 to Campbell et al. which discloses a sewing ring made of a solid PTFE felt ring having a cross-sectional shape of a right triangle. The sewing ring is mounted to a mechanical valve, and one side of the ring extends perpendicular to the flow direction through the valve, thus the right triangle designation. The PTFE felt ring is enveloped by cloth that conforms to the right-triangular shape. When implanted in the mitral position as shown in FIG. 1 of the Campbell patent, the hypotenuse of the right triangle mates with the tissue in the valve annulus.

The design typified by the Campbell patent has a number of significant drawbacks. For example, the solid nature of the PTFE felt ring does not easily conform to an irregularly shaped annulus and introduces an inherent stiffness that limits the ability of the sewing ring to flex with the annulus tissue as that tissue is stressed during normal heartbeat activity. The lack of flexibility or low compliance, in turn, increases the loads exerted on the sutures used to attach the sewing ring potentially leading to leakage problems or damage to the annulus tissue. For example, unduly stiff sewing rings must be sutured in place fairly tightly to prevent perivalvular leakage between sutures. This added tension may strangle the annulus tissue and result in a decubitous ulceration.

The inherent stiffness (low compliance) also severely narrows the margin for error when selecting the appropriate size sewing ring/valve for a given patient. If the selected size is slightly too large, the inability of the PTFE felt ring to easily compress requires undue deformation of the annulus tissue in order to adequately attach the valve. Similarly, if the selected size is slightly too small, the inability of the PTFE felt ring to easily stretch results in undue tension on the tissue and sutures in order to achieve attachment. As a result, a great deal of care and accuracy by the surgeon are needed in the selection of a valve size that precisely matches the valve annulus of the patient. Unfortunately, standard sizing tools are provided in increments based on an overall orifice size, and may not be able to accurately measure a less than optimally formed annulus. The surgeon thus must use informed judgment in selecting an approximate valve size.

The combination of the stiffness in the PTFE felt ring with the right triangle shape also has drawbacks. For example, the valve annulus tissue typically does not have a cross-section which matches the linear hypotenuse, and given the inherently stiff and bulky nature of the PTFE felt ring, there is insufficient flexibility for the hypotenuse edge of the ring to bend in a manner that adequately conforms to the irregular, nonlinear shape of the sculpted annulus cross-section. This again potentially results in perivalvular leakage and tissue damage.

The stiffness/right triangle shape combination also is a limiting factor in providing adequate sewing ring cross-sectional area for suturing (or other attachment methods, e.g., stapling) the valve to the annulus tissue. The annular band of material around the periphery of the sewing ring which serves as the suturing platform is relatively narrow in a radial dimension which necessitates the use of pledgets in conjunction with the sutures. Obviously, the use of pledgets increases the complexity and time required for valve implantation. The annular band of a right triangular sewing ring is so radially narrow that the suture loop passes through a relatively thin portion of the annulus tissue near the annulus tip, and so pledgets must be used.

The implantation problem caused by narrow sewing rings is aggravated in many prior prosthetic valves by rigid structure extending outward from the valve body into the interior of the sewing ring. See, for example, the compressible stiffening ring of Campbell (U.S. Pat. No. 5,397,348). This structure further limits the placement of sutures in the sewing ring to the radially outer regions thereof. Moreover, if attempts were made to increase the annular band of the sewing ring, or to at least increase the cross-sectional angle of the hypotenuse in order to provide a larger suture platform, the solid nature of the PTFE felt ring would only cause an undesirable increase in stiffness and bulkiness. Such a result would then simply amplify the problems already discussed with regard to sewing ring stiffness and low compliance.

In view of the foregoing, it is evident that an improved sewing ring that addresses the apparent deficiencies in existing sewing rings is necessary and desired. That is, there is a need for an advanced design that improves compatibility of the ring to the annulus tissue and simultaneously simplifies for the surgeon the technique used to attach the valve.

SUMMARY OF THE INVENTION

The present sewing ring is designed with a larger radial profile to enable deep passes into the surrounding annulus tissue, and has increased material close to the valve body to enable deep passes into the ring material, both factors enabling a reduction in the number of sutures used. The sewing ring is highly compliant and resilient to better cooperate with movements of the surrounding tissue and accordingly reduce the tension needed for each suture. Moreover, the increased size and novel shapes enable great flexibility in valve placement within the annulus. In short, the present invention provides a sewing ring which is more surgeon-friendly, more secure in preventing leaks, and more flexible.

The present invention addresses deficiencies apparent in the prior art, including improving the coaptation characteristics of the sewing ring and simplifying the surgical methodology for attaching prosthetic heart valves to the valve annulus. In that regard, the present invention provides a novel and non-obvious sewing ring shape and structural makeup that complements the physiological and anatomical characteristics of the annulus and provides an attachment platform that that reduces the need for tedious suturing techniques.

In accordance with the present invention, there is provided a sewing ring that includes a suture-penetrable ring member made of a resilient material that has a plurality of ribs defining adjacent cells or voids that enhance the resiliency of the ring member. The ring member has a radial width that results in the sewing ring providing a coaptation area with the annulus tissue that is sufficiently large so as to enable the attachment of the sewing ring to the annulus tissue without a load distributing device such as a pledget.

In addition, the sewing ring of the present invention combines a resilient ring member with a novel ring member geometry so as to ensure the sufficient coaptation area between the sewing ring and the tissue without unduly stressing the annulus tissue. In the case of a mitral valve implantation, the present invention may include a smoothly contoured blend or coaptation surface to conform to the mitral valve annulus. In the case of an aortic valve implantation, the present invention may include a outwardly extending coaptation side which extends a particular radial distance to ensure the adequate coaptation distance.

Further objects and advantages of the present invention shall become apparent to those skilled in the art upon reading and understanding the following detailed description of a presently preferred embodiment of the invention.

BRIEF DESCRIPTION OF THE DRAWINGS

FIG. 1a is an exploded perspective of a mitral annulus sewing ring in accordance with the present invention showing a mechanical valve in phantom;

FIG. 1b is a perspective assembly view of the mitral annulus sewing of FIG. 1a;

FIGS. 3a–c are schematic cross-sectional views of one side of a mechanical valve and three embodiments of the mitral sewing ring of FIG. 1b;

FIG. 4a is a schematic sectional view of a mitral annulus;

FIG. 4b is a schematic sectional view of a valve sizer in the mitral annulus in preparation for implanting the sewing ring of FIG. 1b;

FIG. 4c is a schematic sectional view of a mechanical valve having the mitral sewing ring of FIG. 1b in the mitral annulus;

FIG. 6a is an exploded perspective view of an aortic annulus sewing ring in accordance with the present invention showing a mechanical valve in phantom;

FIG. 6b is a perspective assembly view of the aortic annulus sewing of FIG. 6a;

FIGS. 9a–c are schematic cross-sectional views of one side of a mechanical valve and three embodiments of the aortic sewing ring of FIG. 6b;

FIG. 10a is a schematic sectional view of an aortic annulus;

FIG. 10b is a schematic sectional view of a valve sizer in the aortic annulus in preparation for implanting an aortic sewing ring similar to that shown in FIG. 6b;

FIG. 10c is a schematic sectional view of a mechanical valve having an aortic sewing ring similar to that shown in FIG. 6b in an aortic annulus;

FIG. 12a is a plan view of a mechanical valve as placed in an intra-annular position in an aortic valve annulus with an fabric covering of an sewing ring of an present invention removed to illustrate an annular sponge similar to that shown in FIGS. 7a or 8a in compression;

FIG. 12b is a top cross-sectional view similar to FIG. 12a with an mechanical valve placed in an supra-annular position in an aortic valve annulus and showing an annular sponge in a relatively uncompressed state;

DESCRIPTION OF THE PREFERRED EMBODIMENTS

Figure 2A:
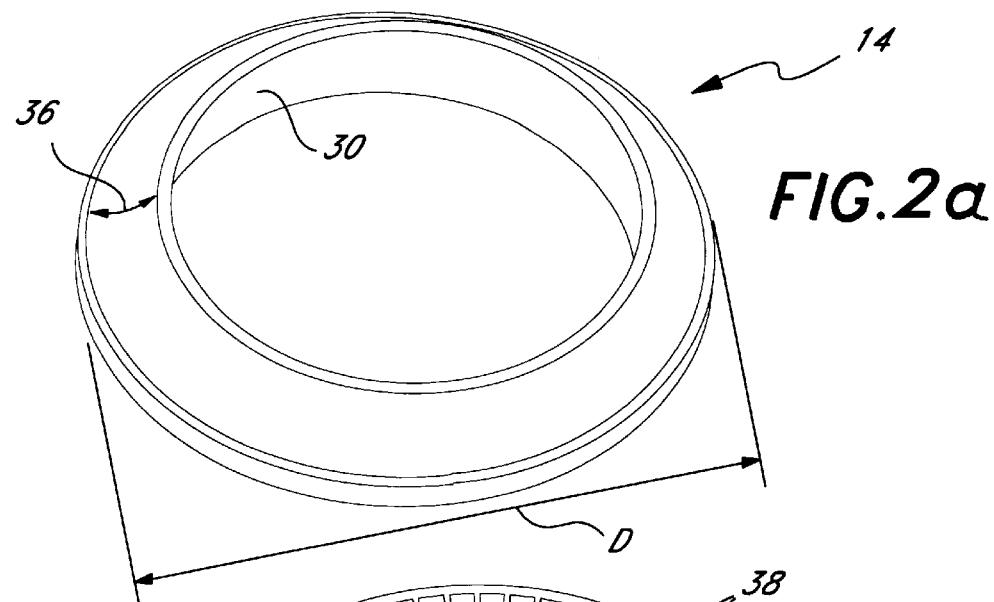
FIGS. 2a and 2b are top and bottom perspective views of a sponge used in a mitral annulus sewing ring in accordance with the present invention.

The detailed description set forth below in connection with the appended drawings is intended as a description of the presently preferred embodiments of the invention, and is not intended to represent the only forms in which the present invention may be constructed or utilized. The description sets forth the structures and functions for the present invention in connection with the illustrated embodiments. It is to be understood, however, that the same or equivalent structures and functions may be accomplished by different embodiments that are also intended to be encompassed within the spirit and scope of the invention.

Preferred embodiments of sewing rings for prosthetic heart valves in accordance with the present invention are disclosed in this description and the Figures. The description and figures include information for using the invention both in mitral valve replacement and aortic valve replacement. However, such description and figures are by way of example only and not by away of limitation. Those skilled in the art will appreciate that the sewing ring of the present invention may be utilized in other various applications.

Mitral Valve Sewing Ring

Referring to FIGS. 1a and 1b, a first embodiment of the present invention generally comprises a sewing ring 10 configured for use with a prosthetic mitral valve MV. The sewing ring 10 generally includes a ring member or stent 12 to which an annular sponge 14 is attachable. A fabric material 16 generally covers the stent 12 and the annular sponge 14. It should be noted that the sewing ring 10 is particularly suited for implantation in the mitral annulus because it conforms to the particular anatomy of that annulus, and valves other than the mechanical valve shown may be used in conjunction therewith. Thus, MV designates mitral valve, whether mechanical or bioprosthetic.

The flow direction of blood though the sewing ring (with the valve MV removed) is seen in FIG. 1b. As used herein, the term proximal refers to that end or edge of the device which is on the upstream or inflow side thereof and the term distal refers to that end or edge of the device which is on the downstream or outflow side of the device. The proximal end of the device is indicated by the letters PE and the distal end of the device is indicated by the letters DE. Notice that the mitral sewing ring 10 expands radially from the outflow or distal end DE to the inflow or proximal end PE. This is because the mitral valve MV is implanted on the inflow side of the mitral annulus from the side of the left atrium.

According to a preferred embodiment of the present invention, the stent 12 is comprised of a polyacetal material, one example of which is DELRIN (a registered trademark of E.I.DuPont DeNemours & Co., Inc. Wilmington, Del.). As those skilled in the art will appreciate, the stent 12 may be comprised of various other polymer materials such as polyacetals, polyesters, ultra high molecular weight polyethylene, polysulfones, polyimides, polyether keytones (e.g., PEEK), liquid crystalline polymers (e.g., LCP's), and/or carbon filter composites. The ring member may alternatively be formed of biocompatible metal or metal alloy, such as titanium Elgiloy or zirconium.

The needle-penetrable fabric material 16 preferably comprises a biocompatible woven or knitted material, such as polyester or other suitable material. The fabric may be treated or coated with various chemical materials/coatings to improve biocompatability (e.g., heparin, chemically bound heparin, carbon coatings, etc.).

The annular sponge 14 is comprised of a biocompatible resilient material, preferably silicone rubber. The needle-penetrable annular sponge 14 preferably comprises a plurality of cells or voids 40 (best shown in FIG. 2b) as described below and is assembled to the stent 12 and fabric material 16 with sutures. More particularly, the stent 12 includes a plurality of apertures 17, preferably two circumferential rows, through which a needle and suture may be threaded. The stent 12 is first attached to the sponge 14, and then the fabric material 16 is wrapped around and covers both entirely, except for an inwardly projecting annular rib 19 (see FIG. 1a) used to secure the assembled ring to the valve body. Such an assembly procedure is described in U.S. Pat. No. 5,755,783 issued May 26, 1998, entitled "SUTURE RINGS FOR ROTATABLE ARTIFICIAL HEART VALVES" and hereby expressly incorporated by reference. Other sewing ring assemblies may be suitable, of course.

Figure 2B:
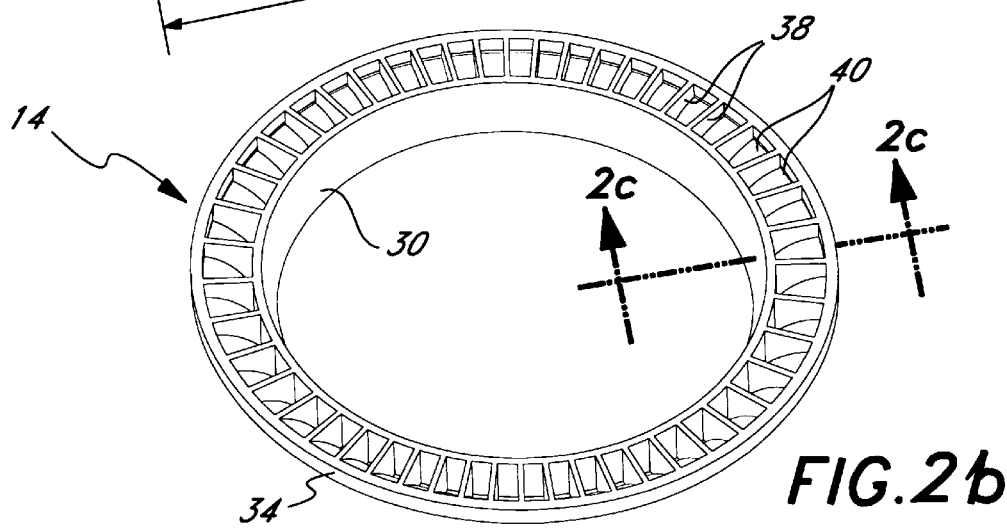
Figure 2C:
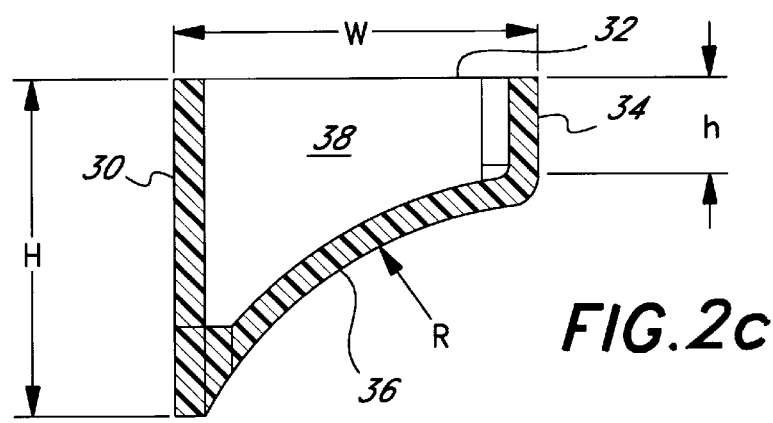
FIG. 2c is a cross-sectional view of the sponge of FIG. 2b as taken along the lines 2c—2c.

Referring more particularly to FIGS. 2a–2c, the annular sponge 14 has a projected cross-sectional configuration characterized by a circumferential inner surface 30 having a dimension H, a radial top surface 32 having a dimension W, a circumferential outer surface 34 having a dimension h, and a smoothly contoured blending surface 36 extending between the bottom ends of the inner surface and the outer surface. The outer surface 34 is substantially smaller than the inner surface 30 and thus defines the periphery of an outwardly extending flange of the sponge 14. The inner surface 30 and outer surface 34 are desirably parallel and axially disposed, although other configurations are possible. A plurality of radially oriented ribs 38 extend between the aforementioned surfaces to divide the interior of the sponge into a plurality of circumferentially arrayed and desirably evenly spaced cells 40. In the illustrated embodiment, discrete walls having faces define the inner surface 30, outer surface 34 and blending surface 36, while the elongated top surface 32 is defined by the top edges of the ribs 38 and is substantially open to the cells 40. In a preferred embodiment, the dimension H of the inner surface 30 is approximately 4.57 mm, the dimension W of the elongated top surface 32 is approximately 4.32 mm, the dimension h of the outer surface 34 is approximately 1.57 mm and the smooth contoured blending surface 36 has a substantially constant radius R of approximately 4.45 mm. The overall diameter D of the annular sponge 14 is seen in FIG. 2a and is generally determined by the size of the annulus into which the sewing ring 10 is received. These dimensions are given as exemplary only, and other dimensions or ranges may be used.

The contoured blending surface 36 may be a curve of constant radius or a complex curve with several different radii of curvature or even an aspheric curve with a constantly changing radius of curvature. The surface 36 desirably mimics as near as possible the ideal shape of a mitral annulus after the natural mitral valve has been excised.

The soft material of the sponge 14 in conjunction with the cells 40 provides a highly compliant sewing ring to facilitate deformation thereof, particularly at the flange or outer surface 34. Such compliance allows the sponge 14 to conform to the sculpted mitral annulus and maximize the valve orifice to annulus ratio. The cells 40 also make the suture ring 10 more easily penetrable by a needle and mitigate dulling of the needle as sometimes occurs with solid PTFE rings.

Mitral Ring Configurations

FIGS. 3a–c illustrate various configurations of the present mitral valve sewing ring on a mechanical valve V for various sized annuluses. Features previously identified such as the stent 12 and sponge 14 will be given like numbers. FIG. 3a shows a sewing ring 10' for use in smaller mitral annuluses having diameters between 23 and 29 mm. The fabric covering typically comprises a long piece 16a on the inflow side and a short piece 16b on the outflow side, the two pieces overlapping on the exterior of the stent 12. Two friction controlling protuberances 42 are provided on the interior of the stent 12 and serve to compress the fabric against the valve body V. FIG. 3b shows a sewing ring 10" for use in mitral annuluses having diameters of approximately 31 mm. The construction is the same as for the sewing ring 10' of FIG. 3a except for a spacer sleeve 44 interposed and sutured between the stent 12 and sponge 14. This sleeve 44 in combination with a larger diameter sponge 14 enables the assembly to fit in larger annuluses. Furthermore, the fabric covering comprises an inflow piece 16a, an outflow piece 16b, and a sponge retainer piece 16c which encompasses the sponge 14 and is secured on the interior thereof. Finally, FIG. 3c shows a valve V and sewing ring 10'" for use in 33 mm annuluses. The construction is identical to the sewing ring 10" of FIG. 3b except for a larger spacer sleeve 46.

Mitral Annulus, Sizing and Implantation

Figure 5A:
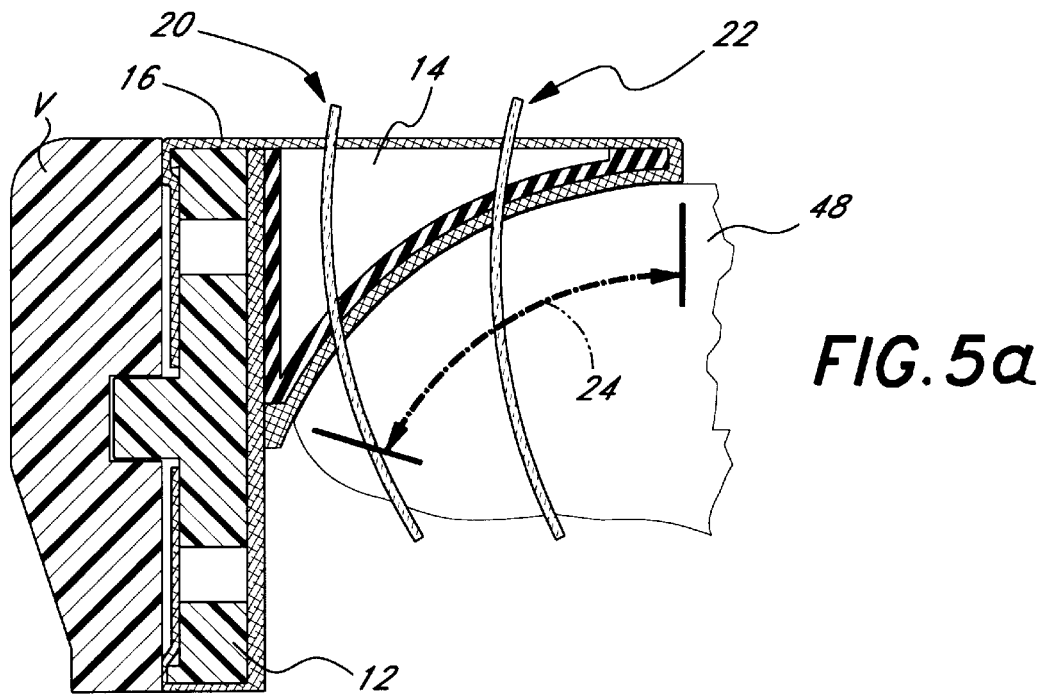
FIG. 5a is a schematic cross-sectional view of one side of a mechanical valve and sewing ring of FIG. 1b placed in a mitral valve annulus.

FIG. 4a schematically illustrates in section a mitral annulus 48 having a diameter X. The well-defined ledge of the mitral annulus 48 may vary depending on the extent of tissue resection required, but is typically more pronounced than the aortic annulus shown in FIG. 10a. FIG. 4b shows a valve sizer 50 shaped like the mitral sewing ring 10 and positioned within the annulus for measurement. When the appropriate sizer is found, the correspondingly sized valve is chosen for implantation. FIG. 4c shows a mechanical valve MV and mitral sewing ring 10 of the present invention as placed into the annulus 48 for implantation. ps Advantages of Mitral Ring The combination of enhanced resiliency due to the plurality of cells 40 with the unique cross-sectional configuration, yields a sewing ring 10 that provides enhanced and increased coaptation with the mitral annulus 48, as best shown in FIG. 5a. It should be noted that the cross-sections such as FIG. 5a illustrating sewing rings attached to annuluses are only schematic, and the precise dimensions may not be to scale. Indeed, the cross-section of the sponge 14 seen in FIG. 2c is accurate, but the cross-section seen in FIG. 5a is not.

Due to the smooth contoured blending surface 36 and the compliance of the multi-celled sponge 14, the sewing ring 10 is able to contact the annulus tissue 48 over substantially all of the blending surface 36 to achieve a substantial coaptation area 24. Moreover, the increased coaptation is achieved without unduly deforming or compressing the tissue. The sizable coaptation area along with the enhanced resiliency improves the stability of the valve during pumping of the heart without damaging the annulus tissue. It also better seals the valve within the annulus to negate the possibility of perivalvular leaking.

It is understood to those skilled in the art that in order to attach a prosthetic mitral valve without pledgets, the surgeon must have a minimum "bite" of about 4 mm of mitral annulus tissue (as measured radially) upon which to introduce and secure the sutures. Such a distance can be gauged from where the annulus tissue touches the outer surface 34 of the sewing ring to where the tissue ends near or at the base of the sewing ring 10. Even if such a bite was available using prior art rings, none had the flexibility and resiliency to deform in cooperation with the tissue and so reduce the stress on each suture. The present mitral rings 10 provide such compliance and resilience in conjunction with the larger shape, and thus enable pledget-free attachment.

Moreover, the unique configuration also yields a suturing platform of sufficient area to allow the introduction of both a ventricular tissue suture 20 in close proximity to the inner periphery of the sewing ring 10 and/or an atrial tissue suture 22 more toward the outer periphery of the sewing ring all without the use of pledgets to distribute the load. In effect, the increased "bite" of the sutures into the annulus afforded by the larger coaptation area 24 enables the tough annulus tissue itself to combat the "cheesewire" effect, thus obviating pledgets. In the alternative, the suturing platform still allows for more traditional horizontal mattress or running sutures, with or without pledgets.

In the preferred embodiment, surgeons are able to reduce the number of sutures used while still ensuring proper sealing around the valve. Desirably, about 20 simple sutures are sufficient to secure the sewing ring 10 to the mitral annulus. This is a decrease of 33% over prior designs which required 30 simple sutures, and represents a decrease of 50% over designs requiring 20 mattress sutures (in effect, doubling the number of passes of simple sutures). Even with the reduced number of sutures, the shape and characteristics of the sewing ring 10 provide adequate protection against subsequent perivalvular leakage. This attractive combination of features is facilitated by the resilient nature of the inner sponge 14 and shape and size of the ring 10. The sutures are passed both deeper into the annulus and deep within the sewing ring to better distribute stresses in tension of the sutures. Between each suture, the sewing ring 10 molds to the annulus tissue whether smooth or irregular. This "hugging" of the annulus is not defeated by beating of the heart and movement of the valve because of the flexible and resilient inner sponge which absorbs such stresses. In short, the soft ring 10 starts out better conforming to the annulus and maintains that conformance at least until tissue ingrowth into the fabric 16 supplants the good seal provided.

Figure 5B:
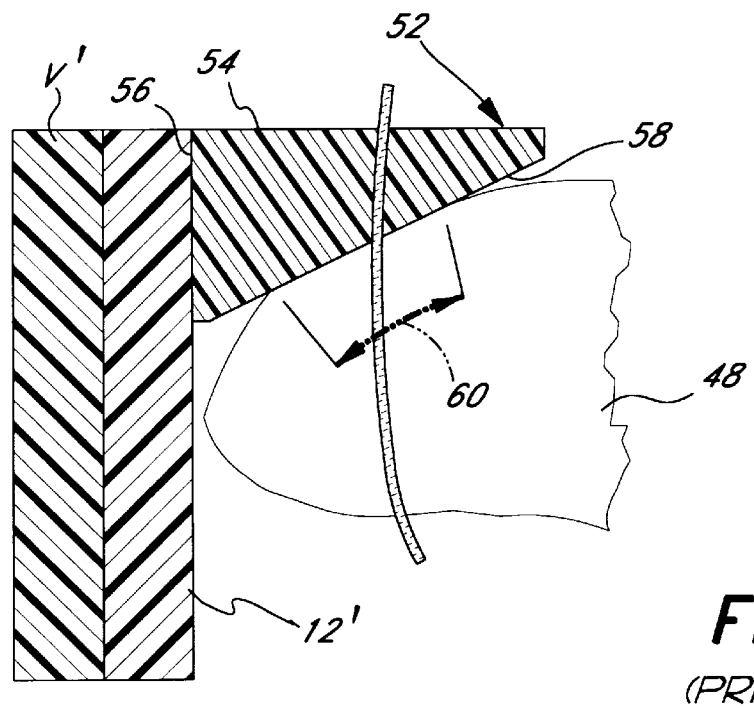
FIG. 5b is a schematic cross-sectional view of one side of a mechanical valve and prior art sewing ring placed in a mitral valve annulus.

The advantages are more clearly seen upon comparison of the sewing ring 10 with a prior art sewing ring 52 depicted in FIG. 5b. The prior art sewing ring 52 is characterized by a solid Teflon felt or cloth filler and has a configuration essentially of a right triangle. The right triangle comprises a top surface 54, an inner surface 56 and a straight edge hypotenuse 58 that connects the top surface 54 and the inner surface 56.

Due to the limited resilience of the solid filler, the edge, 58 contacting the annulus 48 being a straight edge and the dimensions of the sewing ring 52, the tissue 48 and the sewing ring 52 do not coapt to the same advantageous degree offered by the sewing ring 10 of the present invention. Indeed, the coaptation area 60 for the prior art sewing ring 52 is substantially smaller than the coaptation area 24 resulting from the sewing ring 10 of the present invention. And if attempts were made to increase the coaptation area 60, the tissue 48 would become unduly compressed and deformed so as to potentially harm the tissue.

In addition, the prior art sewing ring does not provide a sufficient suturing platform to allow the introduction of sutures 28 without the use of pledgets. The small coaptation area 60 does not provide sufficient tissue interface with the sewing ring to ensure safe attachment of the valve. Pledgets are needed in order to distribute the loads and thereby prevent concentrated loads on the small tissue/sewing ring interface.

Aortic Valve Sewing Ring

Referring to FIGS. 6a and 6b, a second embodiment of the present invention generally comprises a suture ring 110 configured for use with an artificial aortic valve AV. Again, the valve AV may be of a number of types, and is shown as a mechanical valve as an example only. As with the mitral valve configuration discussed above, the sewing ring 110 generally includes a ring member 112 to which an annular sponge 114 is attached. A fabric material 116 generally covers the ring member 112 and the annular sponge 114. The material used for each of the components are the same as those described for the mitral version discussed above.

The sewing ring 110 for use with an aortic valve is generally similar to the sewing ring used for the mitral valve. One exception is that the configuration of the sponge member 114 is generally frusto-conical in shape, thus defining a substantially constant outward taper from the proximal end PE to the distal end DE thereof. Notice that in contrast with the mitral valve of FIGS. 1a and 1b, the aortic sewing ring 110 expands from the inflow or proximal end PE to the outflow or distal end DE. This is because the aortic valve AV is implanted on the outflow side of the aortic annulus. Additionally, the valve body of the aortic valve AV, as well as the sewing ring 110 therefor, are provided in a range of diameters which is less than in the mitral valve because of the smaller aortic annulus.

Figure 7A:
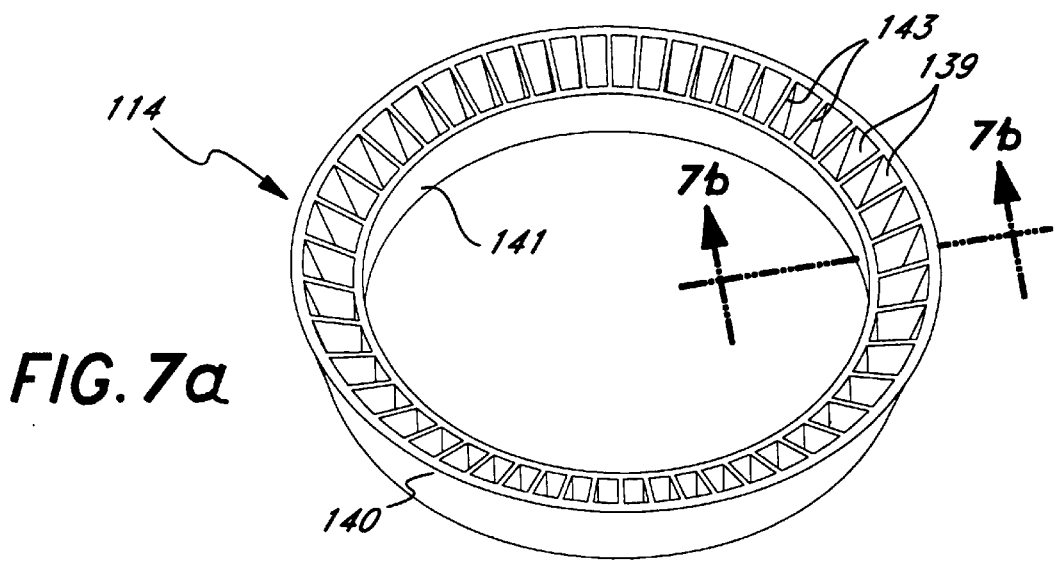
FIG. 7a is a perspective view of a sponge used in an aortic annulus sewing ring in accordance with the present invention.
Figure 7B:
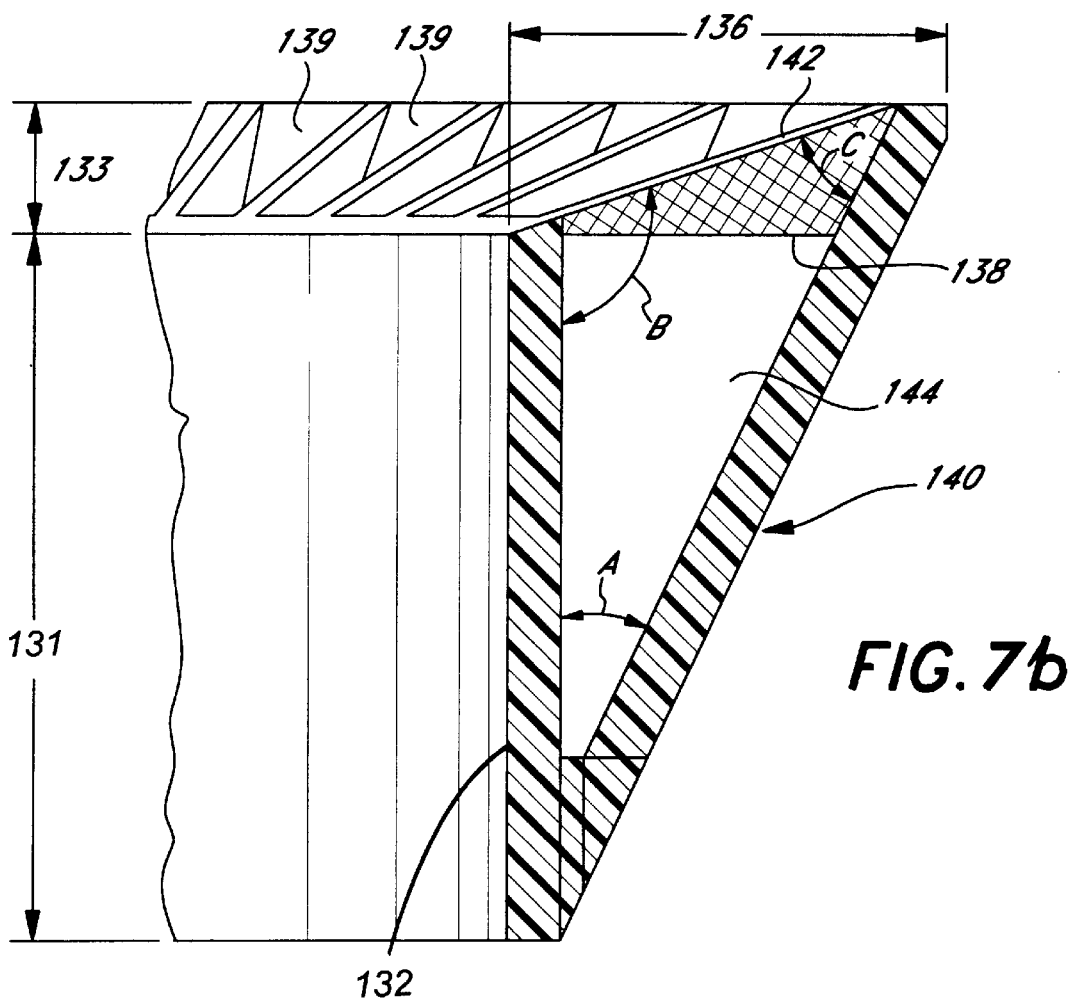
FIG. 7b is a cross-sectional view of the sponge of FIG. 7a as taken along the lines 7b—7b.

Referring to FIGS. 6a, 7a and 7b, the sponge member 114 includes a plurality of cells or voids 139 defined by walls 141 and ribs 143 which provide enhanced flexibility to the sponge member in much the same manner as described with respect to the sewing 14 for the mitral valve. The sponge member 114 has a projected triangular cross-sectional shape defined by three surfaces, namely a coaptation side 140, an inner ring side 132 and a top edge 142 wherein each of the surfaces are separated by an angle A, B and C, respectively. The walls 141 define the coaptation side 140 and inner ring side 132, while the top edge 142 remains open to the cells 139. For larger valves, the lengths of each side and the associated angles are such that the sponge 114 provides a projected triangular area 138 that extends beyond a triangular area 144 that otherwise defines a right triangle within the cross-section of the sponge member 114. As seen in FIGS. 9b and 9c, the triangular area 138 projects past the outflow side or distal end DE of the attached valve body. The coaptation side 140 is desirably shaped to mimic the ideal shape of the aortic annulus after valve excision. The aortic annulus is less pronounced than the mitral annulus, and tends to be 1ass planar and somewhat scallop shaped.

In a preferred embodiment of the ring 110 for larger patients, and with reference to FIG. 7b, the inner ring side 132 has a length 131 of approximately 6.17 mm and the angle A between the inner ring side 132 and the coaptation side 140 is approximately 32.8 degrees. The coaptation side slopes such that it extends a distance 133 beyond the inner ring side 132 of approximately 1.04 mm and then connects with the top edge 142 at an angle C of about 47.2 degrees. The top edge 142 then slopes back to the inner ring side 132 for a horizontal, or radial, distance 136 of approximately 3.18 mm at an angle B of approximately 110 degrees. These dimensions thus lead to the coaptation side 140 having a length of approximately 7.88 mm. Again, these dimensions are exemplary only and should not be construed to limit the invention further than the appended claims.

Once the cloth 116 has been sewed onto the sponge 114, the dimensions will increase accordingly, due to the thickness of the cloth which can range between 0.008 inch (0.20 mm) and 0.014 inch (0.36 mm). The overall projected cross-sectional area of the sewing ring of this preferred embodiment is approximately 10.968 sq. mm. For example, in the preferred embodiment just described, the inner ring side 132 has a length of approximately 6.5 mm and the top edge 136 will have a length of approximately 4 mm.

Rings for Small Aortic Annuluses

Figure 8A:
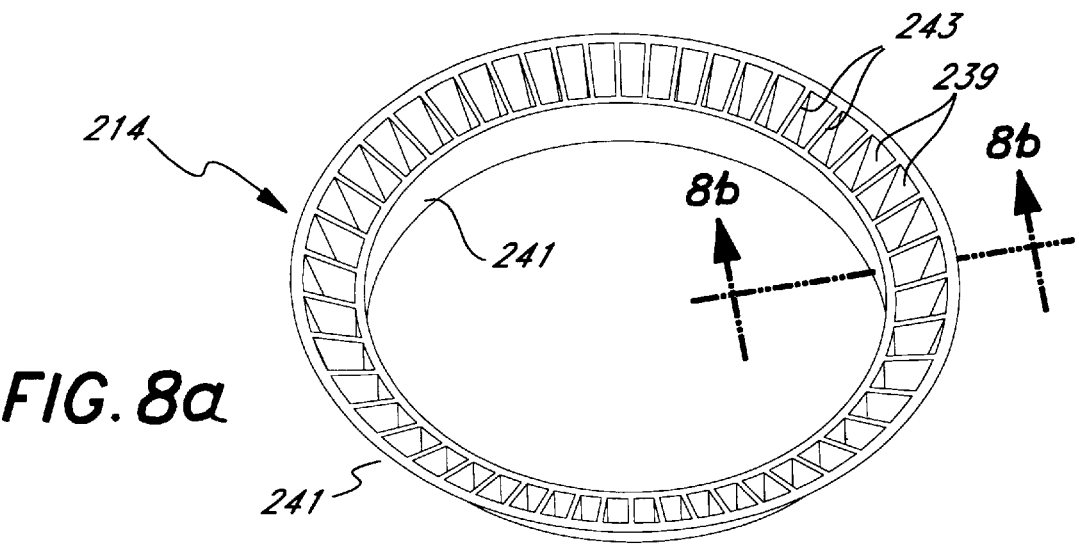
FIG. 8a is a perspective view of a further embodiment of a sponge for use in smaller annulus sewing rings in accordance with the present invention.
Figure 8B:
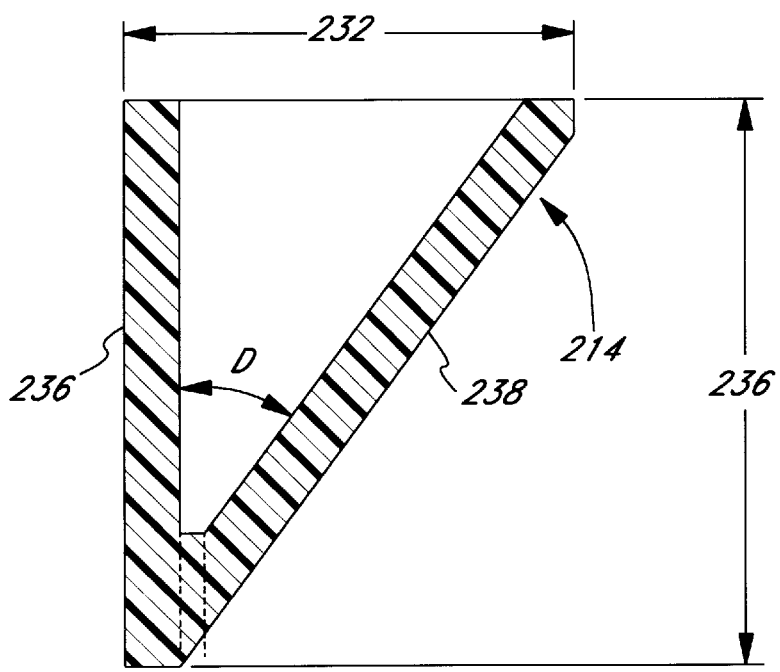
FIG. 8b is a cross-sectional view of the sponge in FIG. 8a taken along the line 8b—8b.

In certain patients, particularly children, the aortic annulus is quite small. As a result, it is sometimes advantageous to utilize a smaller diameter valve and sewing ring (on the order of about 19 mm or 21 mm) that are especially adapted for placement into such a small location. Even with such small annulus diameters, intra-annular placement of a conventionally sized valve would unduly restrict the flow of blood. Consequently, and referring to FIGS. 8*a* and 8*b*, it is advantageous to use a sponge member 214 configured to have a cross-section in the shape of a right triangle but dimensioned so as to maintain increased coaptation with the aortic annulus in the supra-annular position.

As with the sponge described with previous embodiments, the sponge 214 is comprised of cells or voids 239 defined by walls 241 and ribs 243 to enhance the resiliency of the sewing ring 210. In its projected cross-sectional shape, the sponge 214 is configured to have a coaptation side 238, an inner ring side 236 and a top edge 232. The inner ring side 236 and the coaptation side 238 are placed at an angle D from each other.

The top edge 232 has approximately the same length as the corresponding horizontal distance 136 in the sewing ring 114 described previously and in a preferred embodiment, that dimension is approximately 3.18 mm. In the same preferred embodiment, the inner ring side 236 has a length of approximately 3.68 mm and the angle D is equal to approximately 40.4 degrees, thus resulting in a length of 4.865 mm for the coaptation side 238.

Aortic Ring Configurations

FIGS. 9*a*–*c* illustrate various configurations of the present aortic valve sewing ring 110 on a mechanical valve V for various sized annuluses. Features previously identified such as the stent 112 and sponge 114 will be given like numbers. FIG. 9*a* shows a sewing ring 110' for use in smaller aortic annuluses having diameters between 19 and 21 mm. The fabric covering typically comprises a short piece 116*a* on the outflow side and a long piece 116*b* on the inflow side. Two friction controlling protuberances 150 are provided on the interior of the stent 112 and serve to compress one end of the short piece 116*a* and one end of the long piece 116*b* against the valve body V. FIG. 9*b* shows a sewing ring 110" for use in aortic annuluses having diameters of between 21 and 29 mm. The construction is similar to the sewing ring 110' of FIG. 9*a* except the sponge 114 is that shown in FIG. 7*b* which extends above the valve V body. A coaptation face 151 makes a rake angle 152 with a plane 154 normal to the ring axis of between 10° and 20°. More specifically, the rake angle 152 is preferably 10° for 21 mm annuluses and 20° for 23–29 mm annuluses. The coaptation face 151 meets the outer surface of the stent 112 at axial distance 156 of about 1 mm from an inflow end of the valve V. Finally, FIG. 9*c* shows a valve V and sewing ring 110''' for use in 31 mm aortic annuluses. The construction is identical to the sewing ring 110" of FIG. 9*b* except for a consistent rake angle of about 20°. Also, the sponge 114 includes a thickened region 158 at an inflow end which serves to increase the profile of the ring to fit the larger annulus. The region 158 is desirably integrally formed in the silicone sponge 114 and has an axial dimension approximately equal to the axial distance 156 of the smaller ring of FIG. 9*b*.

Mitral Annulus, Sizing and Implantation

FIG. 10*a* schematically illustrates in section an aortic annulus 160 having a diameter X. The aortic annulus 160 is typically less pronounced than the mitral annulus shown in FIG. 4*a* but nevertheless exhibits a datum line 162 at its narrowest orifice. FIG. 10*b* shows a valve sizer 164 shaped like the small diameter aortic sewing ring 110' of FIG. 9*a* and positioned within the annulus for measurement. When the appropriate sizer is found, the correspondingly sized valve is chosen for implantation. FIG. 10*c* shows a aortic valve AV and sewing ring 110' of the present invention as placed supra-annularly with respect to the annulus 160 for implantation.

Aortic Ring Placement Flexibility

One of the advantages in the use of the sponge 114 in the sewing rings 110" or 110''' is that it accommodates aortic valve placement either intra-annularly or supra-annularly without damaging the annulus tissue or adding difficult steps to the surgical methodology. Supra-annularly refers to placement of the valve body generally outside of the annulus itself, while in the intra-annular position the valve body extends substantially within the annulus. And in either application, the sewing ring 110 offers an increased coaptation with the annulus tissue much as described with regard to the mitral valve placement. These advantages are best discussed with reference to FIGS. 11*a*–11*d*.

Figure 11A:
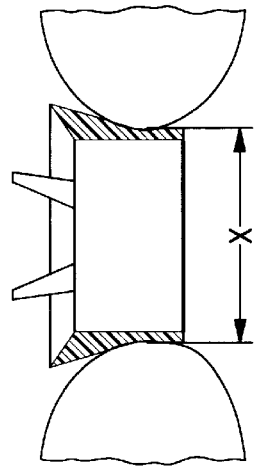
FIG. 11a is a schematic sectional view of a further valve sizer in an aortic annulus in preparation for implanting an aortic sewing ring of FIG. 6b in an supra-annular position.
Figure 11B:
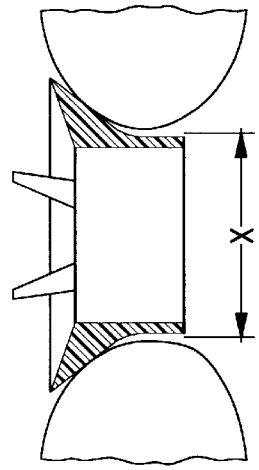
FIG. 11b is a schematic sectional view of an aortic sewing ring of FIG. 6b in an supra-annular position of an aortic annulus.
Figure 11C:
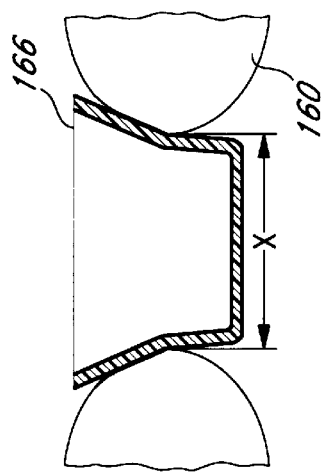
FIG. 11c is a schematic sectional view of an aortic sewing ring of FIG. 6b in an intra-annular position of an aortic annulus.
Figure 11D:
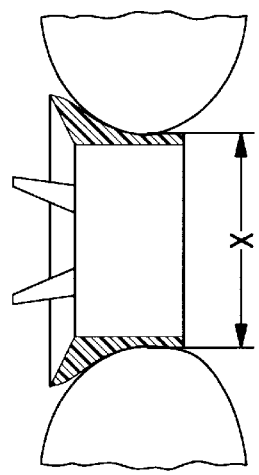
FIG. 11d is a schematic sectional view of a downsized aortic sewing ring of FIG. 6b in an intra-annular position of an aortic annulus.

FIG. 11*a* shows a valve sizer 166 in position in the aortic annulus 160 prior to placement of a valve. The present invention enables the surgeon to take the dimension measured conventionally with the sizer 166 and choose various sized valves depending on the need. That is, conventional wisdom teaches the placement of prosthetic valves intra-annularly to help prevent perivalvular leakage. In some situations, however, a supra-annular placement might be more expedient if not for this leakage potential. FIG. 11*b* shows a mechanical valve and aortic ring 110' or 110''' placed in the supra-annular position. Because of the advantageous shape, compliance, compressibility and resiliency of the present rings, they will conform to the annulus and provide leak free coaptation even in this unconventional position. FIG. 11*c* shows the same valve after being gently manipulated into an intra-annular position. Finally, FIG. 11*d* shows a downsized valve with aortic ring 110' or 110''' of the present invention positioned intra-annularly. The valve may be downsized by 1 or 2 mm based on the surgeon's examination of the needs of the patient. Previous sewing rings were either too stiff and/or not large enough to accommodate all of the various implantation positions that the present rings 110' or 110''' enable.

Sponge Compression

Referring next to FIGS. 12*a* and 12*b*, the configuration of the sponge 114 in the context of either supra-annular or intra-annular implantation is better understood. In FIG. 12*b*, the sponge 114 is shown in the supra-annular position prior to suturing and thus the sponge appears substantially in its undeflected state, at least on the upper end. In FIG. 12*a*, the sponge 14 is shown in the intra-annular position prior to suturing and thus the sponge is deflected in order to account for the smaller annulus size. The ribs 143 dividing the cells 139 are compressed radially inwardly and bend as a result.

Also, the outer peripheral wall 141 of each cell takes on a concave shape. This manner of deflection enables the sewing ring to provide the advantageous resiliency for the sewing ring as previously described. That is, some prior rings provided compliance but no resiliency or spring back. The present ring not only conforms better to the annulus prior to placement, but when placed intra-annularly, for example, springs out to coapt to the tissue.

Advantages of Aortic Ring

Figure 13A:
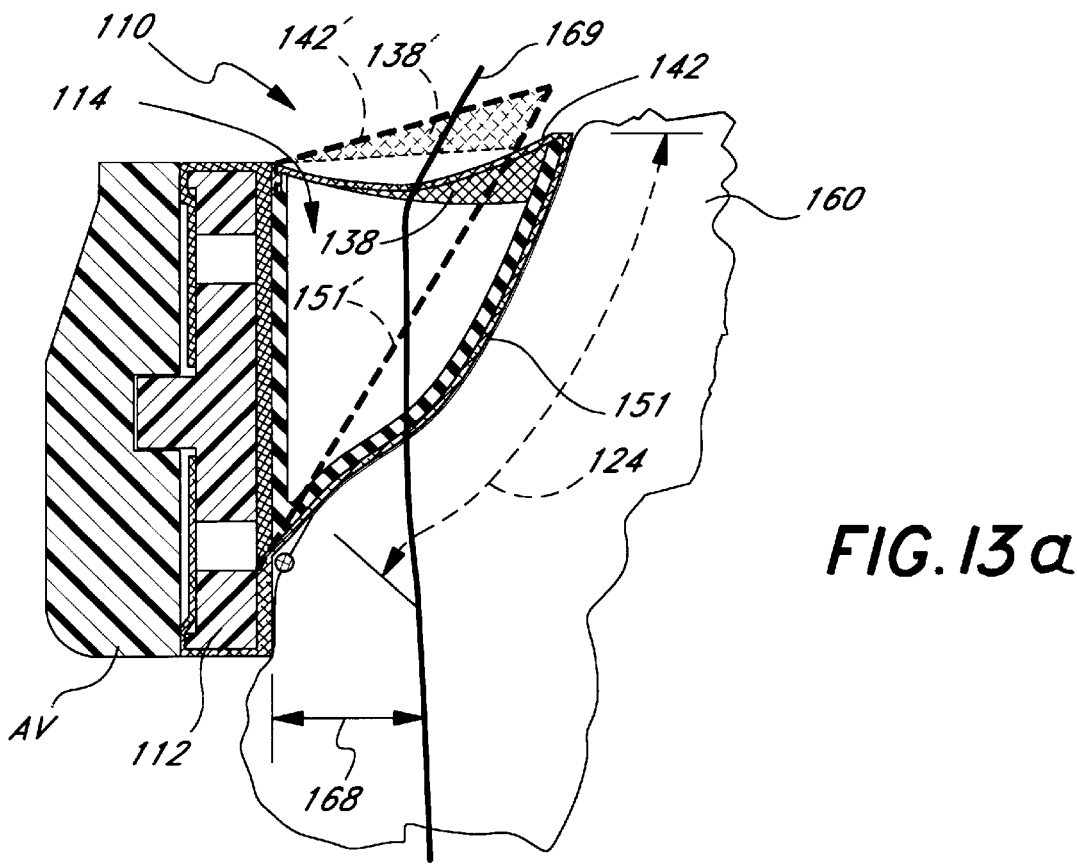
FIG. 13a is a schematic cross-sectional view of one side of a mechanical valve and sewing ring of FIG. 9b or 9c as placed in a supra-annular position in an aortic valve annulus.

The sewing ring 110 (110' or 110'" of FIG. 9b or 9c) placed in the supra-annular position is depicted in FIG. 13a. Prior to being sutured into place, the sewing ring has the undeflected shape as shown by the dotted lines (having element numbers with prime designations), indicating that a significant portion of the sewing ring, including the projected area 138', is not in intimate contact with the tissue 160. In order to secure the sewing ring into place, this portion of the sewing ring 110 must be pulled into engagement with the adjacent tissue 160. Due to the enhanced compliance of the sponge 114, this is easily done as shown by the solid line configuration of the sewing ring without unduly deforming the annulus. The sewing ring 114 is easily pulled into engagement with the tissue without any significant reduction in the length of the coaptation face 151 of the sewing ring I 10 and without any undue stretching being induced in the tissue 160. Furthermore, because of the advantageous cross-sectional area of the sewing ring 110, the coaptation area 124 extends along substantially the entire length of the coaptation face 151 of the sewing ring I 10. Moreover, the coaptation area 124 is substantially equal to the area achieved as if the sewing ring 110 was in its undeflected state.

In addition, due to the geometry of the sewing ring as dictated in large part by the sponge 114, the suturing platform of the sewing ring 110 results in an increased distance 168 between the sewing ring and the location in the tissue 160 in which the surgeon may introduce a suture 169. This increased distance, sometimes termed the "bite", enables suturing the sewing ring to the annulus without using pledgets.

It is understood to those skilled in the art that in order to attach a prosthetic aortic valve without pledgets, the surgeon must have a minimum "bite" of about 3 mm of aortic annulus tissue (measured radially) upon which to introduce and secure the sutures. Such a distance can be gauged from where the aortic annulus tissue touches the periphery of the sewing ring to where the tissue ends near or at the base of the sewing ring 110. Even if such a bite was available using prior art rings, none had the flexibility and resiliency to deform in cooperation with the tissue and so reduce the stress on each suture. The present aortic rings 110 provide such compliance and resilience in conjunction with the larger shape, and thus enable pledget-free attachment.

In addition, the same advantages mentioned above for the mitral ring embodiments are equally applicable to the aortic ring 110. More specifically, less sutures with a better seal are provided along with the elimination of pledgets and the ability to place intra- or supra-annularly. Finally, less tension need be applied to each suture when implanting the valve because of the compliant and resilient nature of the ring 110, thus reducing the potential for decubitous ulceration of the tissue within the suture loop.

Figure 13B:
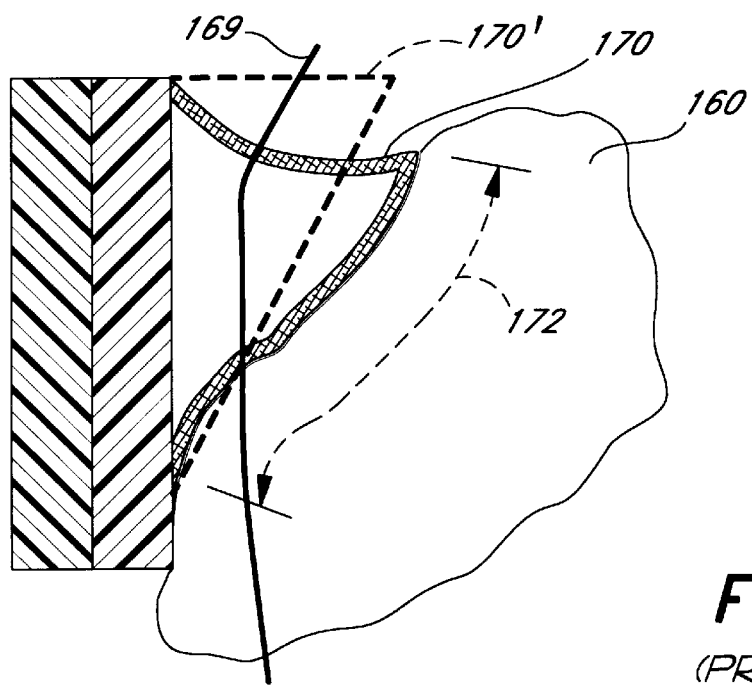
FIG. 13b is a schematic cross-sectional view of one side of a mechanical valve and prior art sewing ring as placed in an supra-annular position in an aortic valve annulus.

These advantages are better understood with reference to FIG. 13b which shows the use of a prior art aortic annulus sewing ring 170 made of either solid Teflon felt or cloth filler as positioned in the supra-annular position. The prior art sewing ring does not have the necessary resiliency to allow attachment of the sewing ring to the tissue below without significantly deforming the sewing ring and inducing undue stretching forces on the tissue 160. Moreover, the geometry of the sewing ring 170 is such that the available coaptation area is already limited and becomes even more so when the sewing ring is deformed in order to achieve attachment with the tissue. As is seen the coaptation area 172 is much less than the coaptation area 124 achieved with the sewing ring 110 of the present invention. As a result, the surgeon is left with smaller amount of tissue upon which to attach the sewing ring 170, thus necessitating the use of pledgets.

Figure 14A:
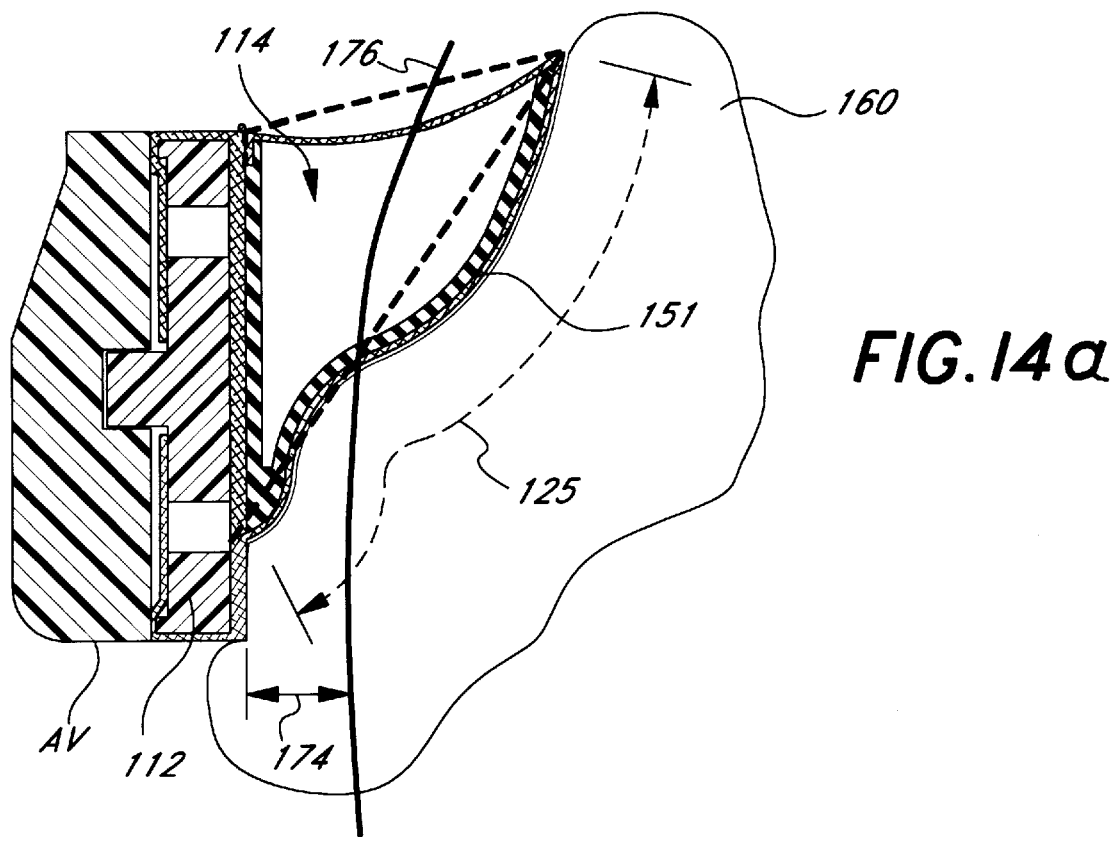
FIG. 14a is a schematic cross-sectional view of one side of a mechanical valve and sewing ring of FIG. 9b or 9c as placed in an intra-annular position in an aortic valve annulus.

The sewing ring 110 (110" or 110'" of FIG. 9b or 9c) placed in the intra-annular position is depicted in FIG. 14a. Prior to suturing, the sewing ring 110 must be delicately manipulated and eased into the annulus by the surgeon (hence, "intra-annular" placement) since the annulus for such placement is smaller in diameter than the outer diameter of the sewing ring. Due to the enhanced resiliency of the sewing ring 110, such placement is achieved without adversely compressing the surrounding annulus tissue 160 and without unduly compressing the sewing ring so as to lose coaptation area. In fact, the enhanced resiliency enables the sewing ring 110 to better match the contour of the annulus tissue and thus further enhance the coaptation. The enhanced resiliency combined with the sewing ring geometry thus results in a coaptation area 125 that is substantially the same as what would be obtained if the coaptation face 151 was in the undeflected state. As discussed above, this combination also results in an increased bite 174 for the surgeon to introduce a suture 176 without using a pledget.

Figure 14B:
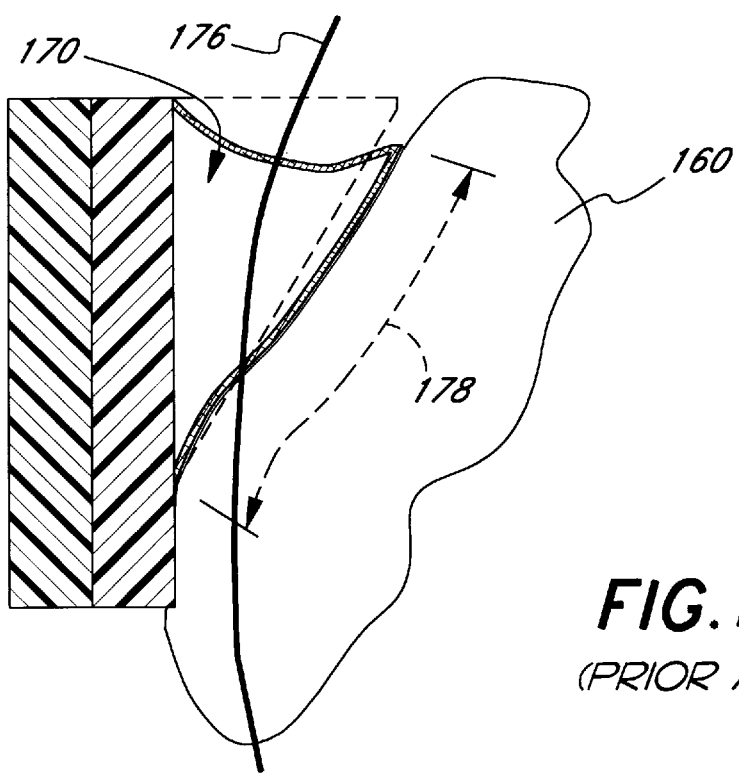
FIG. 14b is a schematic cross-sectional view of one side of a mechanical valve and prior art sewing ring as placed in an intra-annular position in an aortic valve annulus.

The advantages in the intra-annular placement context are better understood with reference to FIG. 14b which depicts the same prior art sewing ring 170 as discussed with respect to FIG. 13b. Due to the limited resiliency of the sewing ring 170, the tissue 160 is unduly compressed when the ring is positioned into intra-annular position. This makes the step of placing the valve more difficult for the surgeon. In addition, the geometry of the sewing ring 170 as compared to the sewing ring 110 of FIG. 14a yields a coaptation area 178 that is significantly less than the coaptation area 125 offered by the sewing ring 110 of the present invention.

The following Table I is a comparison of sizes of various sewing rings available on the market and one example of the sewing ring of the present invention. The sewing rings have the following sources:

A—Carbomedics Inc. of Houston, Tex.

B—St. Jude Medical of Minneapolis, Minn.

C—Baxter Healthcare Corp. of Irvine, Calif. (Starr)

D—Baxter Healthcare Corp. of Irvine, Calif. (TEKNA)

E—Present invention

TABLE I

COMPARISON OF SUTURABLE AREAS

| SEWING RING | A | B | C | D | E |
|---|---|---|---|---|---|
| USABLE RADIAL WIDTH* | 1.5 mm | 2.0 mm | 3.3 mm | 2.5 mm | 4.06 mm |
| USABLE CROSS-SECTIONAL AREA | 3.9 mm$^2$ | 4.0 mm$^2$ | 10.3 mm$^2$ | 5.2 mm$^2$ | 11.0 mm$^2$ |
| COMPOSITION | SOLID CLOTH | SOLID CLOTH | SOLID SILICONE SPONGE | CELLED SILICONE SPONGE | CELLED SILICONE SPONGE |

*The term "usable radial width" is that width extending radially outward from the valve body or stent structure through which sutures can be passed. This term takes into account any obstruction to the passage of sutures on the valve body or stent structure which decreases the absolute width of each ring.

The term "usable radial width" is that width extending radially outward from the valve body or stent structure through which sutures can be passed. This term takes into account any obstruction to the passage of sutures on the valve body or stent structure which decreases the absolute width of each ring.

None of the aforementioned prior art sewing rings offers the combination of enhanced resiliency with the unique geometry of an aortic sewing ring in accordance with the present invention, nor the increased coaptation between the sewing ring and the annulus tissue.

It is understood that the examples and embodiments described herein and shown in the drawings represent only the presently preferred embodiments of the invention, and are not intended to exhaustively describe in detail all possible embodiments in which the invention may take physical form. Indeed, various modifications and additions may be made to such embodiments without departing from the spirit and scope of the invention.

What is claimed is:

1. A sewing ring for use in implanting a prosthetic heart valve to a support annulus, comprising:

a suture-penetable annular ring member formed of a plurality of deformable walls, some of which are radially aligned to define open cells therebetween, the annular ring member being oriented about an axis and having a top end and a bottom end spaced along the axis, the annular ring member having a cross section defined by an axially extending inner ring side, a top side projecting radially outward from the top end of the inner ring side, and a coaptation side extending between an outermost projection of the top side and the inner ring side, wherein the coaptation side is at least partly concavely curved and is defined by one of the deformable walls to thereby provide a concavely curved tissue coaptation surface around the periphery of the ring that compliantly conforms to the support annulus and resists perivalvular leaking therebetween; and a fabric covering surrounding at least an outer portion of the annular ring member.

2. The sewing ring of claim 1, wherein the coaptation side is defined as a curve of a constant radius.

3. The sewing ring of claim 2, wherein the constant radius is approximately 4.45 mm.

4. The sewing ring of claim 1, wherein the coaptation side is formed as a complex curve with more than one radius of curvature.

5. The sewing ring of claim 1, wherein the coaptation side is formed as an aspheric curve with a constantly changing radius of curvature.

6. The sewing ring of claim 1, wherein the top side projects directly radially outwardly from top end of the inner ring side a distance of at least about 3.18 mm.

7. The sewing ring of claim 6, wherein the top side projects radially outwardly a distance of about 4.32 mm.

8. The sewing ring of claim 6, wherein the coaptation side is defined as a curve of a constant radius at least as great as the distance the top side projects radially outwardly.

9. The sewing ring of claim 1, wherein the fabric covering is treated with a chemical to improve biocompatibility.

10. The sewing ring of claim 9, wherein the chemical comprises heparin.

11. The sewing ring of claim 1, wherein the annular ring member comprises silicone rubber.

12. A heart valve, comprising:

the sewing ring of claim 1;

a rigid annular valve body; and an annular stent intermediate the valve body and sewing ring.

13. The valve of claim 12, wherein the fabric covering surrounds both the annular ring member and at least a portion of the annular stent, and extends partway between the stent and valve body.

14. The valve of claim 13, wherein the fabric covering is in two pieces, a first piece around the inflow end of the stent and annular ring member and a second piece around the outflow end of the stent.

15. The valve of claim 14, wherein a portion of the second piece extends between the stent and annular ring member.

16. The valve of claim 14, wherein the first piece is longer than the second piece.

17. The valve of claim 12, further including a spacer sleeve positioned between the annular stent and annular ring member.

18. The valve of claim 17, wherein a first portion of the fabric covering completely surrounds the annular ring member, and a second portion surrounds the annular stent and spacer sleeve, the second portion extending between the stent and valve body and between the spacer sleeve and annular ring member.

19. The valve of claim 18, wherein the second portion is in two pieces, a first piece around the inflow end of the stent and spacer sleeve and a second piece around the outflow end of the stent and spacer sleeve.

20. The valve of claim 19, wherein the two pieces of the second portion overlap between the spacer sleeve and annular ring member.

21. The valve of claim 20, wherein the first piece is shorter than the second piece.

* * * * *